US00PP23611P2

(12) United States Plant Patent
Hurd

(10) Patent No.: US PP23,611 P2
(45) Date of Patent: May 21, 2013

(54) ***VERONICA* PLANT NAMED 'SWEET LULLABY'**

(50) Latin Name: *Veronica*
Varietal Denomination: Sweet Lullaby

(75) Inventor: Kevin A. Hurd, Chicago, IL (US)

(73) Assignee: Walters Gardens, Inc., Zeeland, MI (US)

( * ) Notice: Subject to any disclaimer, the term of this patent is extended or adjusted under 35 U.S.C. 154(b) by 160 days.

(21) Appl. No.: 13/135,549

(22) Filed: Jul. 8, 2011

(51) Int. Cl.
*A01H 5/00* (2006.01)

(52) U.S. Cl.
USPC ..... Plt./251

(58) Field of Classification Search ..... Plt./251
See application file for complete search history.

*Primary Examiner* — Annette Para

(57) ABSTRACT

The new and distinct cultivar of ornamental Spiked Speedwell plant *Veronica* 'Sweet Lullaby' with erect compact spikes of numerous light pink flowers above low mats of foliage and suitable as a potted plant, the garden, attracting hummingbirds, and for cut flower arrangements.

1 Drawing Sheet

Botanical classification: *Veronica*.
Variety denomination: 'Sweet Lullaby'.

BACKGROUND OF THE INVENTION

The present invention relates to the new and distinct cultivar of Spiked Speedwell, botanically known as *Veronica* 'Hocus Pocus', and hereinafter referred to as the cultivar 'Hocus Pocus' or the "plant". The new plant referenced as breeder code 05-05 and was hybridized in the summer of 2005 by Kevin A. Hurd at a nursery in Zeeland, Mich., USA, as an open pollination of *Veronica* 'Giles Van Hees' (not patented). The plant has been asexually propagated by shoot tip cuttings at the same nursery in the greenhouses in Zeeland, Mich., with subsequent asexually propagated plants found to be identical to the original selection with all the same traits as the original seedling.

BRIEF SUMMARY OF THE PLANT

*Veronica* 'Sweet Lullaby' is unique from all other Spiked Speedwell known to the inventor. Other forms have white, lavender, blue or pinkish lavender flowers, but this is the only variety known by the applicant to have two-tone ruby and white flowers. The closest comparison varieties known to the applicant are: *Veronica* 'Pink Damask' (not patented), *Veronica* 'Giles Van Hees' (not patented), *Veronica* 'Pink Eveline' U.S. Plant Pat. No. 18,743, *Veronica* 'Tickled Pink' U.S. Plant Pat. No. 16,182, *Veronica* 'Atomic Pink' U.S. Plant Pat. No. 21,797, *Veronica* 'Pink Panther' U.S. Pat. No. 16,311, *Veronica* 'Foxy Lady' U.S. Plant Pat. No. 20,679 and *Veronica* 'Red Fox'. *Veronica* 'Atomic Pink' has more purple in the flower compared to the new plant. 'Foxy Lady' has a two-tone bright fuchsia and white flower, and 'Giles Van Hees', Pink Damask', 'Pink Eveline', 'Pink Panther', 'Red Fox' and 'Tickled Pink' are have deeper pink flowers than 'Sweet Lullaby' with 'Red Fox' the deepest and 'Pink Panther' and 'Tickled Pink' the lighter pink flowers in the group. 'Pink Panther' and 'Tickled Pink' are still deeper pink than 'Sweet Lullaby'. 'Pink Panther' is much taller, and 'Tickled Pink' is much less erect in scape, tending to be more floppy and horizontal than the new plant. The plant differs from the female parent, 'Giles Van Hees', in having a much lighter pink flower.

VERONICA COMPARISON

| Cultivar | Petal Color | Scape Height |
|---|---|---|
| 'Atomic Pink' | purple-violet | 40 to 45 cm |
| 'Foxy Lady' | bright fuchsia and white | 25 to 30 cm |
| 'Giles Van Hees' | bright pink | 15 to 20 cm |
| 'Pink Damask' | rose pink | 60 to 90 cm |
| 'Pink Eveline' | bright pink | 35 to 40 cm |
| 'Pink Panther' | medium pink | 50 to 55 cm |
| 'Red Fox' | fuchsia pink | 30 to 35 cm |
| 'Sweet Lullaby' | light pink | 25 to 28 cm |
| 'Tickled Pink' | deep pink | 15 to 20 cm |

The following are traits of *Veronica* 'Sweet Lullaby' that in combination distinguish it from all other known Spiked Speedwell:

1. Stiff, upright, compact spikes above short mats of foliage.
2. Numerous compact flowers of distinctly light pink petals.

BRIEF DESCRIPTION OF THE DRAWINGS

The photograph is of a greenhouse-grown two-year old specimen of the new plant and demonstrates the unique traits and the overall appearance of 'Sweet Lullaby'. The colors are as accurate as reasonably possible with color reproductions. Variation in ambient light spectrum, source and direction may cause the appearance of minor variation in color.

FIG. 1 shows the plant in full flower.

DETAILED BOTANICAL DESCRIPTION

The following descriptions and color references are based on the 2001 edition of The Royal Horticultural Society Colour Chart except where common dictionary terms are used. *Veronica spicata* 'Sweet Lullaby' has not been observed under all possible environments. The phenotype may vary slightly with different growing environments such as temperature, light, fertility, soil pH, moisture and maturity levels, but without any change in the genotype. The following observations and size descriptions are based on two-year old greenhouse-grown plants at a nursery in Zeeland, Mich. with supplemental fertilizer and water as needed.

Botanical classification: *Veronica.*

Parentage: Female or seed parent *Veronica* 'Giles Van Hees' (not patented); male or pollen parent unknown.

Plant habit: Hardy herbaceous perennial, compact, with several branched stems, 8 to 10 cm tall without scapes, 25 to 28 cm tall with scapes and 30 to 35 cm wide just above soil level; flowering beginning late June in Michigan and continuing for about four weeks with occasional repeat if deadheaded.

Leaves: Simple, lanceolate, opposite, serrated, minutely pubescent above and below, acute apex, cuneate base; blade about 5.5 cm long by 1.4 cm wide decreasing in size distally.

Leaf color: Darker than RHS 137A on top, nearest RHS 137C below.

Petiole: Simple, concaved upward on edges, minutely pubescent above and below; about 1.5 cm long and 1.0 mm wide.

Petiole color: RHS 137A above and RHS 137C below.

Venation: Reticulate; depressed above and protruding beneath, minutely pubescent below and above; main center vein about 0.5 mm diameter.

Vein color: Nearest RHS 138A on top or adaxial surface; center vein and secondary veins closest to center vein on abaxial surface between RHS 144A and RHS 146C.

Buds two days prior to opening: Convolute, narrowly oblong, obtuse apex; about 5 mm long and 2.0 mm diameter.

Bud color: Nearest RHS 62B at apex and lightening to lighter than RHS 62D toward base.

Flowers: On upright spikes branched at nearly every node on the main scape and some secondary nodes; numerous, approximately 160 per main inflorescence and 60 in the larger secondary inflorescences; about 7 mm in diameter and about 6 mm deep; no detectible fragrance; flowers persist individually for 4 to 6 days whether on the plant or cut, self-cleaning.

Petals: Four, simple, entire, surface slightly shiny, with rounded to obtuse apex and fused at base; about 6 mm long by 2 mm wide, glabrous outer and inner sides except with 1 mm long at inside base.

Petal color: Distal portion between RHS 62D and RHS 65D on both adaxial and abaxial sides, petal base lighter than RHS 62D on adaxial and abaxial sides with a terminal portion less than 0.5 mm long of nearest RHS N144B; hairs in inside throat of lighter than RHS 62D.

Androecium:

*Filaments.*—Two, fused to lower portion of petal; about 4.0 mm by less than 0.2 mm, lighter than RHS 145D with slight tinting of RHS 76D.

*Anther.*—Dorsifixed with anther ends bent back around filament in about 270 degrees; each half elliptic with acute apex, about 1.5 mm by 1.0 mm, nearest RHS 174D.

*Pollen.*—Abundant, globose, less than 0.1 mm; nearest RHS 10B.

Gynoecium:

*Style.*—8.0 mm by 0.25 mm, RHS 64A toward apex and gradually lightening to lighter than RHS 62D at base.

*Stigma.*—Cylindrical, 0.25 mm in diameter; persists after petals drop; RHS 64A.

*Ovary.*—Spherical, about 1.0 mm diameter, nearest RHS 144A; Sepals; four, surface dull, ovate to narrowly ovate, acute apex, base fused forming corolla, glabrous, upper pair about 2 mm long and 0.5 mm wide, lower pair about 3 mm long by about 0.5 mm wide, RHS 137A abaxial surface and RHS N138C adaxial surface.

Peduncle: About 30 per plant; raceme, strong, erect, round, sparsely canescent; about 25 to 28 cm long and 3 mm in diameter at base, flowering section of the main stem about 13 cm long; diameter at flowering portion of raceme about 2 cm; branched at nearly every node, about seven nodes, nodes about 2.25 cm apart.

Peduncle color: Between RHS 144A and RHS 144B.

*Pedicel.*—Upright, rigid, rounded, sparsely canescent, subtended by minutely pubescent bract of about 3 mm long and 1.0 mm diameter.

Pedicel color: Between RHS 144A and RHS 144B.

Bract: One, subtending each flower, linear, acute apex, mostly entire, sessile, based fused to peduncle, proximal bracts about 2 cm long and 4 mm wide and decreasing distally to about 2 mm long and less than 0.5 mm wide.

Bract color: RHS 137A above and RHS 137C below.

Fruit: Elliptic, less than 1 mm long; between RHS 166A and RHS 166B.

Propagation: The plant roots from cuttings in about 2 weeks and finishes to flowering in a 3.8 liter container in 8 to 10 weeks following a vernalization period of about 8 weeks.

Hardiness, pest and disease resistance: The plant grows best with plenty of moisture and adequate drainage, but is able to tolerate some drought when mature. Hardiness at least from USDA zone 4 through 8. Disease and pest resistance beyond what is typical of that of other Spiked Speedwell has not been observed.

I claim:

1. A new and distinct plant cultivar of ornamental Spiked Speedwell, *Veronica* 'Sweet Lullaby', as herein described and illustrated, with erect compact spikes of numerous light pink flowers above low mats of foliage and suitable as a potted plant, the garden, attracting hummingbirds, and for cut flower arrangements.

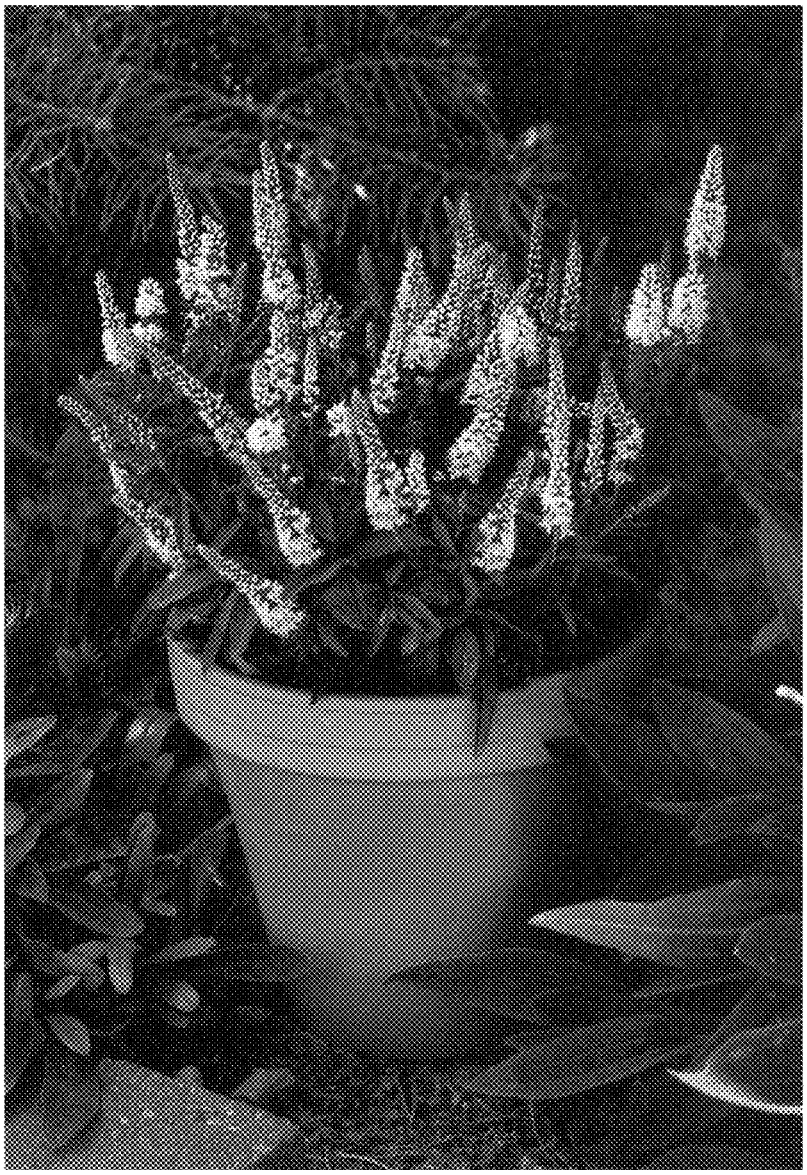

* * * * *